United States Patent [19]                  [11] Patent Number: 4,827,910
Mathews, III                                [45] Date of Patent: May 9, 1989

[54] LARYNGOSCOPE

[76] Inventor: Malcolm R. Mathews, III, 226 Crown Prince Dr., Marlton, N.J. 08053

[21] Appl. No.: 122,327

[22] Filed: Nov. 18, 1987

[51] Int. Cl.$^4$ ............................................. A61B 1/06
[52] U.S. Cl. ................................... 128/11; 128/207.15
[58] Field of Search ....................... 128/10, 11, 3, 4, 6, 128/207.15, 12–16

[56] References Cited

U.S. PATENT DOCUMENTS

| | | | |
|---|---|---|---|
| 1,433,705 | 12/1947 | Palmeter | 128/10 |
| 4,245,465 | 10/1981 | Racz et al. | 128/11 |
| 4,360,008 | 11/1982 | Corazzelli | 128/11 |
| 4,592,343 | 6/1986 | Upsher | 128/11 |
| 4,611,579 | 9/1986 | Bellhouse | 128/11 |

Primary Examiner—Richard C. Pinkham
Assistant Examiner—Mark S. Graham
Attorney, Agent, or Firm—Paul M. Denk

[57] ABSTRACT

Whereas the mouth, pharynx and larynx can be inspected by direct vision or by indirect mirror vision, the most widely used instrument for personal endoscopy is the laryngoscope. Through the years many modifications have been made to improve laryngoscopes. But in considering laryngoscope improvements it should be understood that frequently the instrument is employed in emergency situations where the length of time taken to insert the laryngeal blade is critical. Improvements which demand careful manipulation, and thereby result in loss of valuable seconds, are not the most desirable. By this invention a laryngoscope blade which comprises upwardly extending appendages at either side of the tip of the blade and a jog between the appendages such that a fork-like guide is formed is provided which can be more rapidly introduced. This construction facilitates moving the epiglottis forwardly, and provides a better view of the trachea. It also shortens endotracheal intubation time.

4 Claims, 1 Drawing Sheet

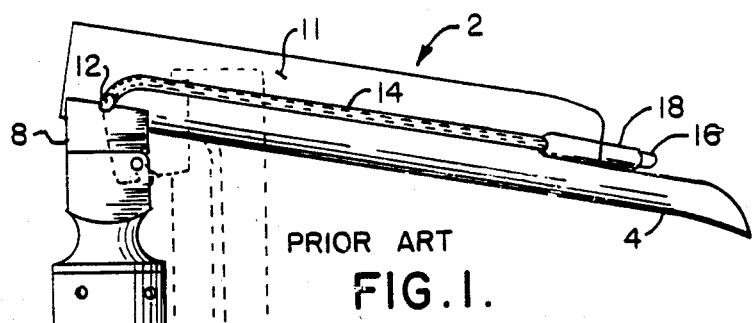
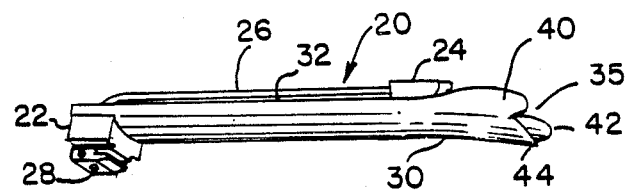
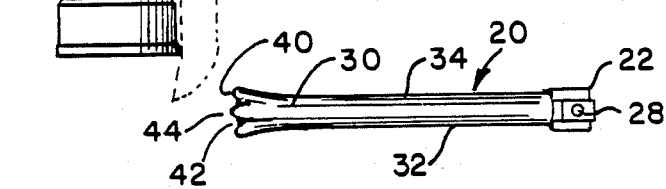
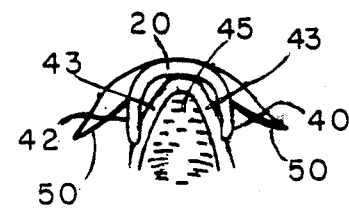
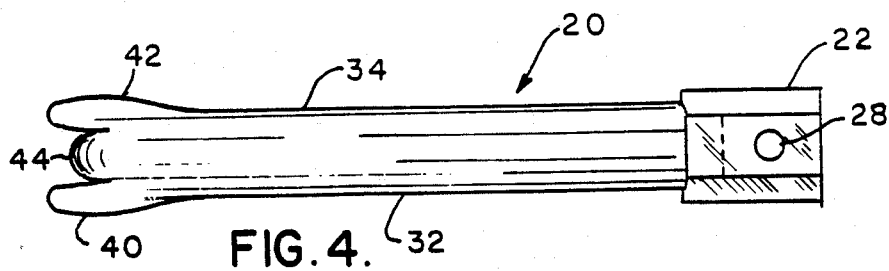
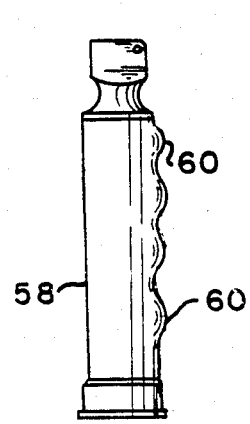
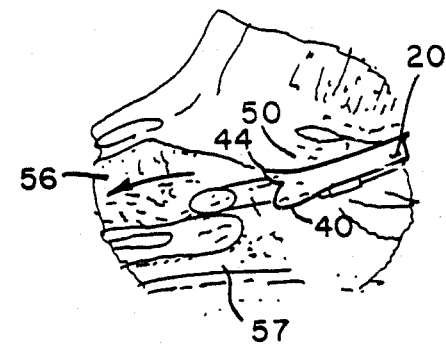

LARYNGOSCOPE

BACKGROUND OF THE INVENTION

This invention is concerned with laryngoscopy, and particularly with improvements in laryngoscopes. In a more specific aspect the invention is directed to an improved laryngoscope blade.

Even though laryngoscopes were popularized by Magill over fifty years ago they are neverless in wide use today. Whereas the mouth, pharynx and larynx can be inspected by direct vision or by indirect mirror vision, it is only Possible to view the inner surfaces of the trachea and bronchi by peroral endoscopy. The most widely used instrument for peroral endoscopy is the laryngoscope.

In addition to endoscopy and inspection of the larynx, laryngoscopy is in frequent use in anesthesiology and in emergency medicine. Even though the introduction of anesthetics is most easily carried out by an intravenous administration, the use of endotracheal tubes is often necessary. Tracheal intubation requires the use of a laryngoscope. In addition the administration of anesthetics calls for reliable monitoring and control of ventilation. In emergency medicine laryngoscopy is not infrequently necessary for the diagnosis or removal of upper airway obstructions, and for tracheal intubation. Laryngeal tubes are also used, with simultaneou ventilation and anesthesia, if microsurgery in the region of the larynx is necessary. Laryngoscopy is thus quite common, even apart from emergency demands.

Through the years modifications have been made to improve Magill's straight blade laryngoscope. For example, by U.S. Pat. No. 2,433,705, (FIG. 1 herein) a light was added for better vision.

The laryngoscope light was improved by the invention of U.S. Pat. No. 4,592,343. A new light source was mounted so that it could be used with a conventional laryngoscope blade. The patent also shows a curved blade. Curved laryngeal blades are not as widely used as straight blades. Not only must they be inserted in the vallecula, but usually at some point during their introduction the curvature or hump obliterates the view.

In U.S. Pat. No. 4,360,008 a laryngoscope is provided having an adjustable distal end tip. The tip is selectively manually adjustable so that it can be disposed in any convenient angle relative to the main blade portion. With this pivotal tip soft tissue in the laryngeal area, such as the epiglottis, can be selectively displaced.

A different type of laryngoscope blade is shown in U.S. Pat. No. 4,573,451. This laryngoscope has a bendable or flexible tip. It is characterized as being easier to insert into a patients throat. It can be longitudinally pivoted with respect to the main body of the blade to move the epiglottis so as to expose the larynx.

It is to be emphasized that the use of a laryngoscope requires some surgical technique or experience. It is not easy to move the epiglottis forwardly while being careful not to injure the vocal cords. In U.S. Pat. No. 4,611,579 this problem is recognized. In order to make introduction easier, the laryngoscope blade of U.S. Pat. No. 4,611,579 is in the form of two components. They are joined at an angle of about 135 degrees to each other. The ratio of the length of one component to the length of the other is in the range of 4:5 to 4:3.

In considering laryngoscope improvements it should be understood that frequently this instrument is employed in emergency situations where the length of time one takes to insert the laryngeal blade is critical. Improvements which demand careful manipulation, and therefore result in loss of valuable seconds, are not the most desirable. Prolonged laryngoscope introduction which extends anoxia during the process is serious, and can be fatal. Laryngoscopes which do not function well under all conditions have not been widely accepted. By this invention a laryngoscope blade is provided which, like the prior art blades, is easier to use. It can also be more rapidly introduced. In addition it affords an advantage not considered by others, that of improving endotracheal intubation.

SUMMARY OF THE INVENTION

As indicated, this invention is concerned with a laryngoscope of the type having a detachable straight blade and a handle therefor. The blade is a one-piece, elongated blade having a distal end capable of being introduced into a patient's laryngeal area. The other end is adapted to be detachably connected to the handle. Being straight, the blade has no longitudinal curvature, but it does have upwardly curved sides forming a channel the length of the blade. This longitudinal channel forms a path through which a patient's glottic opening can be seen as the introduction end of the blade is inserted into the laryngeal area. In one of its aspects this invention is directed to an improvement of such a straight laryngeal blade which provides an enhanced view of the glottic opening, particularly of the vocal cords. Even more important, it includes means facilitating moving the epiglottis forwardly for viewing and intubation. It also provides means shortening endotracheal tube intubation time.

DETAILED DESCRIPTION OF THE INVENTION

The larynx is susceptible to trauma, injury, and various diseases, which must be treated. Laryngoscopes are employed in such treatments. In addition laryngoscopes are used in general anesthesia and emergency medicine. Hence even though known for years, laryngoscopes are still extensively used. Accordingly improvements to them, such as those contemplated herein, are highly significant. These improvements can be better understood by an explanation of them in conjunction with the accompanying drawings.

FIG. 1 is a side view of a prior art laryngoscope showing the instrument's general features.

FIG. 2 is a perspective view of a laryngoscope blade of this invention.

FIG. 3 is a bottom view of the same laryngeal blade.

FIG. 4 is a bottom view showing a different form of laryngeal blade of the invention.

FIG. 5 is a representation of a laryngoscope handle improved by this invention.

FIG. 6 shows a view of the laryngeal area as seen through the laryngeal blade of the invention.

FIG. 7 shows the use of my laryngeal blade in intubation.

For an understanding of the general features of known laryngoscopes, attention is drawn to FIG. 1. Broadly, a laryngoscope 2 consists of a strong blade member 4, carried by a usual handle 6. During use, the blade is almost perpendicular to the handle as shown in FIG. 1. Hence except when stowed, blade 4 projects outwardly from handle 6, at this angle, or at an angle slightly less than perpendicular, in order to open a patient's airway. Usually blade 4 and handle 6 are detachably connected so that the handle can be removed for sterilization. In general this connection includes a detachable hinge connection 8. With this hinge connection 8 the laryngeal blade 4 can be folded or collapsed as illustrated by the broken lines in FIG. 1. In this state the laryngoscope can be conveniently included in a medical bag without removing the blade.

Desirably handle 6 will be the type containing dry cells (not shown) as a source of electrical energy. Hinge connection 8 includes an electrical contact such as 28 in FIGS. 2, 3, and 4. This contact is electrically connected at 12 to line 14, powering electric lamp 16 in socket 18 for better viewing of the laryngeal cavity.

As indicated the use of a laryngoscope requires technique and practice, particularly under limited visibility and stressful emergency conditions. Extreme care must be exercised during the introduction of the laryngeal blade in order to avoid damaging pillar, sulcus and other pharyngeal tissue. At the same time the teeth must not be used as a fulcrum. More important, the laryngoscope blade must be quickly introduced in order to avoid such complications as hypoxia, emesis, aspiration, and arrhythmia. Rapid introduction is extremely vital if the Patient is not breathing. Such patients can be brain dead in four minutes. With the time taken for blade introduction being critical improvements which make it faster are very desirable. It will also be appreciated that the laryngoscope it already does. In U.S. Pat. No. 4,611,579 it is stated that where it is difficult to expose the larynx the anesthetist must go to the corner of the mouth and insert the laryngoscope blade laterally to the incisor teeth. The instrument is moved over the anterior pillar of the tonsil, and then into the sulcus between the tongue and the tonsil. If the laryngoscope blade tip cannot be controlled, the introduction or insertion of the blade is much more difficult. This invention is concerned with that introduction problem. The invention encompasses an improved laryngoscope which is not only easier to insert beneath the epiglottis, but which can be more rapidly introduced because of the improved visibility of the field.

Laryngoscope blades 20 of this invention are shown in FIGS. 2, 3, and 4. As can be seen, the blade includes the conventional means 22 for connecting it to the laryngoscope handle. It also includes the usual light 24. As is known, an electric line 26 connects light 24 to electrical contact 28 in connecting means 22. The electricity is conducted from a battery source in handle 6 as noted hereinbefore.

Referring to FIGS. 2 and 3, it will be appreciated that the blade 20, from its connecting means 22 to its distal end 30 is straight. The blade is, however, curved from side to side as shown in FIG. 6. This cross-sectional curvature, formed by upwardly extending side walls 32 and 34, results in a channel 35 the length of the laryngeal blade, through which the glottic opening can be viewed.

It is emphasized that even though connecting end 22 of the laryngoscope blade is conventional, the distal end 30, which is introduced into the laryngeal aperture, is not. This introduction end 30 is provided with tabs 40 and 42, and jog 44 therebetween. In addition there is no conventional overhanging side ledge such as side ledge 11 shown in FIG. 1.

In FIG. 2 it can be seen that tabs 40 and 42 are Petaloid appendages which extend or protrude above the sides of blade 20. Jog 44, on the other hand, is a projecting or retreating element between tabs 40 and 42. Petaloid tabs 40 and 42 prohibit the doctor from advancing the blade toward the vocal chords without lifting the laryngoscope upwardly to clear the throat. This lifting action provides a view of the laryngeal area which resembles that illustrated in FIG. 6. Laryngeal blade 20 holds back the epiglottis 50 exposing the vocal cords 43 and trachea 45. An examination of FIG. 6 shows the epiglottis 50 being held back so that petaloid tabs 40 and 42 form a sight aperture through which the vocal cords 43 can be better seen.

On being able to see the glottic opening through the sight aperture, the laryngoscope can be more rapidly advanced. During this introduction the straight laryngeal blade is inserted between a patient's upper and lower teeth while the patient's mouth is held open. The laryngeal blade is advanced to the left side of the mouth, displacing the tongue to the right. At this point the physician can sight through the aperture rather than merely down the blade to view the glottic opening before the blade is advanced any further. While continuing to view the glottic opening through the aperture the blade is advanced. Greater care can be exercised using the laryngoscope of this invention to ensure that the laryngeal blade does not injure the oropharynx, hypopharynx and nasopharynx surfaces. At the same time the blade tip must be inserted just beneath the epiglottis 50 without using the teeth. By the provision of jog 44 this invention also makes the tip easier to insert beneath the epiglottis. In the blade jog 44 is formed between tabs 40 and 42, but it has an edge or lip as shown in FIG. 4 which drops away from the blade. In the position in which it is introduced jog 44 desirably curves upwardly away from the plane of the blade. This renders it easier to insert under the epiglottis in order to displace the epiglottis anterioraly.

The importance of the time gained by the use of jog 44 and the sight aperture can be appreciated when the importance of adequate ventilation and oxygenation ar considered. In fact, perhaps the most important aspect of this invention is the use of the laryngoscope blade contemplated herein in endotracheal intubation. Endotracheal intubation is the insertion of a tube into the larynx, using a laryngoscope to directly visualize the vocal cords. It is well known that during endotracheal intubation one may be able to see the larynx, but still be unable to guide the intubation tube through the vocal cords. In such instances it is necessary to insert a wire guide in the endotracheal tube. This of course takes time, which is of the essence. Endotracheal intubation, including the introduction of the laryngoscope, must be accomplished in the time one can hold one's breath. This makes the laryngeal blade herein highly expedient. This aspect of the invention is exemplified in FIG. 7. In FIG. 7 the laryngoscope blade 20, its tab 40 and its jog 44 are readily apparent, as is epiglottis 50. In fact, from FIG. 7 one can imagine how epiglottis 50 can shut off trachea 56 while food passes into esophagus 57.

Normally the tip of a laryngoscope blade is of no use in endotracheal intubation because the tube slips off of it. The endotracheal tube cannot be controlled by the blade tip of a conventional laryngoscope. By this invention the Ushaped tip of the laryngoscope blade can be used to guide the endotracheal tube. As seen in FIG. 7 the endotracheal tube is on its way into trachea 56. The laryngeal blade tip functions as a fork in guiding the tube, the prongs being tabs 40 and 42. During intubation the tabs keep the intubation tube from sliding off as it is being advanced and guided between the vocal cords. If a conventional laryngeal blade were used, the tube would tend to roll off of its tip.

Heretofore there has been no relationship between an endotracheal tube and the size of the laryngeal blade channel. By this invention the blade channel side walls (32 and 34) have upward curvatures coincident with the external curvature of the endotracheal tube. In contrast with prior art blades, this U-shaped channel allows the tube to slide within its channel as shown in FIG. 7.

There are circumstances, such as cervical spinal cord injuries, and altered consciousness, where a patient's head and neck should not be moved. In these instances nasotracheal intubation is indicated. Nasotracheal intubation is even more difficult than oral intubation. The physician, in effect, is working blind in guiding the endotracheal tube through the vocal cords. Textbooks on medicine suggest that if all maneuvers fail, and nasotracheal intubation is still deemed the method of choice, the endotracheal tube can be inserted into the larynx using a laryngoscope to see by, and intubation forceps to guide the tube. This technique, besides being cumbersome, endangers cartilage and soft tissue. The laryngeal blade of this invention provides a method for overcoming blind intubation. The endotracheal tube is maneuvered to a tip of a straight laryngeal blade provided with a U-shaped or V-shaped slot formed by the tabs and jog in accordance with this invention. Using the U-shaped slot, while visualizing the glottic opening, the tube end is advanced and directed so that it passes the vocal cords.

It can be seen that the invention herein solves three Problems known to exist in larynogscopy. The laryngoscope blade herein is easier to insert under the epiglottis. It provides an improved visualization channel. It also facilitates endotracheal intubation. Given these teachings, variations will occur to those in the field. Thus, the edges of tabs 40 and 42 can be thickened or rolled to mitigate their effect on soft cartilage tissue. In addition, so long as they extend above sides 32 and 34 of channel 35, the tabs can be variously shaped. (See FIG. 4.) Further, so long as the jog between the tabs extends away from the plane of the blade, it can project, recede, or have a straight edge. Moreover it can be provided with a lip as shown in FIG. 4. Still further, in cross section the blade tip can be U or V shaped, with the distance across its walls being slightly greater than the diameter of an endotracheal tube.

Other modifications are possible in the visualization components. With the introduction of fiberoptics various lights are available for such instruments. In addition, prisms, and lenses can be used. Another preferred modification is shown in FIG. 5. During blade insertion using a laryngoscope, the teeth must not be used as a fulcrum. The modification shown in FIG. 5 makes this less likely. To make it easier to lift the epiglottis the laryngoscope handle 58 is provided with knurls 60. The inclusion of these ridges, or finger grooves, resembling a gun grip or bicycle grip, makes it easier to raise the instrument without pressing against the teeth. Such ramifications are deemed to be within the scope of this invention.

What is claimed is:

1. In a laryngoscope with a straight blade having an attachment end adapted to be detachably connected to a handle, a distal (insertion) end adapted to be inserted into a patient's laryngeal area, and upwardly curved sides, the improvement comprising tabs in the form of petaloid appendages on the insertion ends of the upwardly curved sides to expedite blade introduction, the petaloid appendages protruding upwarding above the blade sides so that one appendage can elevate the epiglottis higher than usual as the other appendage rests on the hypopharynx opposite the epiglottis making a wider than normal pharyngeal opening for a better view of the vocal chords and trachea, and so that it prohibits a user from advancing the blade toward the vocal chords without lifting it, and a blade tip in the form of a jog between the petaloid appendages with slots therebetween forming a fork-like guide to direct an endotracheal tube into the glottic opening during intubation.

2. The laryngoscope of claim 1 wherein each petaloid tab has an upwardly bowed curvature conforming to the curvature of the upwardly curved blade side to which it is joined.

3. The laryngoscope of claim 2 wherein the channel side walls have upward curvatures coincident with external curvature of an endotracheal tube so that such a tube is slidable in that channel during intubation.

4. The laryngoscope of claim 1 having a handle affording better leverage including ridges and finger grooves forming a handle grip.

* * * * *

UNITED STATES PATENT AND TRADEMARK OFFICE
CERTIFICATE OF CORRECTION

PATENT NO. : 4,827,910

DATED : May 9, 1989

INVENTOR(S) : Mathews, Malcolm R., III

It is certified that error appears in the above—identified patent and that said Letters Patent is hereby corrected as shown below:

Claim 1, column 6, line 25, change "upwarding" to ---upwardly---.

Signed and Sealed this

Twenty-sixth Day of December, 1989

Attest:

JEFFREY M. SAMUELS

Attesting Officer     Acting Commissioner of Patents and Trademarks